United States Patent [19]

Gutman

[11] 4,020,161
[45] Apr. 26, 1977

[54] THIOLOPHOSPHORAMIDATES AND THEIR USE AS INSECTICIDES

[75] Inventor: Arnold D. Gutman, Berkeley, Calif.

[73] Assignee: Stauffer Chemical Company, Westport, Conn.

[22] Filed: Mar. 31, 1976

[21] Appl. No.: 672,191

[52] U.S. Cl. ............................ 424/211; 260/944; 260/950; 424/217
[51] Int. Cl.² ...................... A01N 9/36; C07C 9/24
[58] Field of Search ........... 260/950, 944; 424/211, 424/217

[56] References Cited

UNITED STATES PATENTS

| | | | |
|---|---|---|---|
| 3,825,632 | 7/1974 | Pallos | 260/944 |
| 3,826,830 | 7/1974 | Pallos | 260/944 X |

*Primary Examiner*—Anton H. Sutto

*Attorney, Agent, or Firm*—Joel G. Ackerman

[57] ABSTRACT

Compounds having the formula

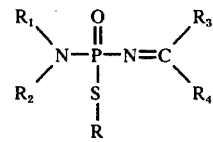

in which R and $R_1$ are lower alkyl, $R_2$ and $R_3$ are independently lower alkyl or hydrogen, provided that at least one of $R_2$ and $R_3$ is lower alkyl, and $R_4$ is amino or lower alkoxy. The compounds have utility as insecticides and/or acaricides.

20 Claims, No Drawings

THIOLOPHOSPHORAMIDATES AND THEIR USE AS INSECTICIDES

DESCRIPTION OF THE INVENTION

This invention relates to certain novel thiolophosphoramidates and their use as insecticides. More particularly, this invention relates to certain novel compounds having the formula $$\begin{array}{c} R_1 \\ \diagdown \\ R_2 \end{array} N-\underset{\underset{\underset{R}{|}}{\overset{\overset{O}{\|}}{P}}-N=C}{\overset{}{\underset{}{|}}}\begin{array}{c} R_3 \\ \diagup \\ \diagdown R_4 \end{array}$$

in which R and $R_1$ are lower alkyl, $R_2$ and $R_3$ are independently lower alkyl or hydrogen, provided that at least one of $R_2$ and $R_3$ is lower alkyl, and $R_4$ is amino or lower alkoxy.

By terms "lower alkyl" and "lower alkoxy" are meant such groups containing from 1 to about 6 carbon atoms, preferably from 1 to 3 carbon atoms, for instance methyl, ethyl, n-propyl, isopropyl, methoxy, ethoxy, and the like. In a preferred embodiment of the invention, R is methyl.

In another aspect, the invention also relates to a process or method for controlling insects by applying to the insect or the habitat thereof an insecticidally effective amount of a compound having the formula $$\begin{array}{c} R_1 \\ \diagdown \\ R_2 \end{array} N-\underset{\underset{\underset{R}{|}}{\overset{\overset{O}{\|}}{P}}-N=C}{\overset{}{\underset{}{|}}}\begin{array}{c} R_3 \\ \diagup \\ \diagdown R_4 \end{array}$$

in which R and $R_1$ are lower alkyl, $R_2$ and $R_3$ are independently lower alkyl or hydrogen, provided that at least one of $R_2$ and $R_3$ is lower alkyl, and $R_4$ is amino or lower alkoxy. By the term "insects" as used herein, is meant to include acarids or mites. By the term "insecticidally effective amount" as used herein is meant to include an amount of the compound which is effective against either insects or acarids.

The compounds of the present invention are prepared in general by the following method:

A dialkylamidophosphorothiochloridate is treated with gaseous ammonia in an inert solvent and the product is rearranged by refluxing it in methyl iodide to form a thiolo phosphorodiamidate:

$$\begin{array}{c} R_1 \\ \diagdown \\ R_2 \end{array} N-\underset{\underset{OR}{|}}{\overset{\overset{S}{\|}}{P}}-Cl + NH_3 \longrightarrow \begin{array}{c} R_1 \\ \diagdown \\ R_2 \end{array} N-\underset{\underset{OR}{|}}{\overset{\overset{S}{\|}}{P}}-NH_2$$
$$\text{(I)} \qquad\qquad\qquad \text{(II)}$$

$$\xrightarrow{CH_3I} \begin{array}{c} R_1 \\ \diagdown \\ R_2 \end{array} N-\underset{\underset{SR}{|}}{\overset{\overset{O}{\|}}{P}}-NH_2$$
$$\text{(III)}$$

The product is then reacted with an orthoester to produce the final imidate product.

$$\begin{array}{c} R_1 \\ \diagdown \\ R_2 \end{array} N-\underset{\underset{SR}{|}}{\overset{\overset{O}{\|}}{P}}-NH_2 \xrightarrow{(R_4O)_3-C-R_3} \begin{array}{c} R_1 \\ \diagdown \\ R_2 \end{array} N-\underset{\underset{SR}{|}}{\overset{\overset{O}{\|}}{P}}-N=C\begin{array}{c} R_3 \\ \diagup \\ \diagdown R_4 \end{array}$$

Amidine compounds ($R_4$=$NH_2$) are produced by reacting the imidate with ammonia $R_1R_1$, $R_2$, $R_3$ and $R_4$ are as defined above.

The following examples demonstrate the preparation of compounds of the present invention:

EXAMPLE 1

Preparation of the intermediate N,N-dimethyl-S-methylthiolophosphorodiamidate.

19.2 g(0.102 mole) O-methyl-N,N-dimethylamidophosphorothiochloridate (I, R, $R_1$, $R_2$ = methyl) and 100 ml acetonitrile were combined in a 250 ml flask and saturated with ammonia. The reaction was conducted at room temperature. After completion of the reaction, the mixture was filtered and the filtrate evaporated to yield 15 g of II (R, $R_1$, $R_2$ = methyl). This was refluxed for 6 hours with 25 ml of methyl iodide, which was then stripped off. The residue was treated with 200 ml of methylene chloride- hexane solution (80:20), filtered and the filtrate evaporated in vacuo to yield 12.2 g of N,N-dimethyl-S-methylthiolophosphorodiamidate (intermediate III, R, $R_1$, $R_2$ = methyl), $n_D^{30}$ 1.5480.

EXAMPLE 2

Preparation of S-methyl-N,N-dimethyl-N'-(O-ethyl formylidene) thiolophosphorodiamidate (compound 1 herein)

4.0 g (0.026 mole) of compound III prepared as in Example 1 was combined in a 100 ml flask with 7.4 g (0.05 mole) triethyl orthoformate, 25 ml acetonitrile and 0.5 ml alcoholic HCl. The mixture was heated until boiling ceased. The reaction mass was then stripped of solvent to yield 4.3 g of the desired product, $n_D^{30}$ 1.4820.

EXAMPLE 3

Preparation of N,N-dimethyl-S-methyl-N'(Δ-ethoxypropylidene) thiolophosphorodiamidate (compound 3 herein)

In the same manner as in Example 2, there were combined 7.7 g (0.05 mole) compound III, 13.2 g (0.075 mole) triethyl orthopropionate, 25 ml acetonitrile and 0.5 ml alcoholic HCl. There was obtained 8.9 g of the desired product, $n_D^{30}$ 1.5030.

EXAMPLE 4

Preparation of N-(N',N'dimethylamino-S-methyl-thioloamidophosphoryl) propionamidine (compound 5 herein)

5 g (0.021 mole) of compound 3, prepared by the foregoing Example, was dissolved in 5 ml ethanol. The solution was saturated with ammonia gas and, when the temperature returned to ambient, the mixture was stripped to yield 4.5 g of the desired product, $n_D^{30}$ 1.4965.

The following Table I lists representative compounds of the present invention which may be prepared according to the above procedures.

Table I

| Compound No. | R | $R_1$ | $R_2$ | $R_3$ | $R_4$ | $n_D^{30}$ |
|---|---|---|---|---|---|---|
| 1 | $CH_3$ | $CH_3$ | $CH_3$ | H | $OC_2H_5$ | 1.4820 |
| 2 | $CH_3$ | $CH_3$ | $CH_3$ | $CH_3$ | $OC_2H_5$ | 1.4873 |
| 3 | $CH_3$ | $CH_3$ | $CH_3$ | $C_2H_5$ | $OC_2H_5$ | 1.5030 |
| 4 | $CH_3$ | $CH_3$ | $CH_3$ | H | $OCH_3$ | viscous oil |
| 5 | $CH_3$ | $CH_3$ | $CH_3$ | $C_2H_5$ | $NH_2$ | 1.4965 |
| 6 | $CH_3$ | $CH_3$ | $CH_3$ | H | $NH_2$ | 1.5167 |
| 7 | $CH_3$ | $i-C_3H_7$ | H | $CH_3$ | $OC_2H_5$ | 1.4965 |

Insecticidal Evaluation Tests

The following insect species were used in the evaluation tests for insecticidal activity.
1. Housefly (HF) — Musca domestica (Linn.)
2. German Roach (GR) — Blatella germanica (Linn.)
3. Lygus Bug (LB) — Lygus hesperus (Knight)
4. Bean Aphid (BA) — Aphis fabae (Scop.)
5. Salt Marsh Caterpillar (SMC) — Estigmene acrea (Drury)
6. Tobacco Budworm (TBW) — Heliothis virescens (F.)

The insecticidal evaluation tests were conducted as follows:

Housefly: Test compounds were diluted in acetone and aliquots pipetted onto the bottom of 55 × 15 mm aluminum dishes. To insure even spreading of the chemical on the bottom of the dishes, 1 ml of acetone containing 0.02% peanut oil was also added to each dish. After all solvents had evaporated, the dishes were placed in circular cardboard cages containing 25 female houseflies, one to two days old. The cages were covered on the bottom with cellophane and on the top with tulle netting, and each contained a sugar-water saturated cotton plug for maintenance of the flies. Mortality was recorded after 48 hours. Test levels ranged from 100 µg/25 female houseflies down to that at which approximately 50% motality occurred. The LD-50 values are expressed below in Table II under the heading "HF", in terms of µg of the test compound per 25 female flies.

German Cockroach: Test compounds were diluted in a 50—50 acetone-water solution. 2 cc of the solution were sprayed through a DeVilbiss type EGA hand spray gun into circular cardboard cages containing 10 one-month-old German cockroach nymphs. The test cages were covered on the bottom with cellophane and on the top with tulle netting. Percent mortality was recorded 7 days later. Test concentrations ranged from 0.1% down to that at which approximately 50% mortality occurred. LD-50 values are expressed below in Table II under the heading "GR" in terms of percent of the test compound in the sprayed solution.

Lygus Bug: Test compounds were diluted in a 50—50 acetone-water solution. 2 cc of the solution were sprayed through a DeVilbiss type EGA hand spray gun into circular cardboard cages containing 1 string bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD-50 values are expressed below in Table II under the heading "LB" in terms of percent of the test compound in the sprayed solution.

Black Bean Aphid: Nasturtium plants (Tropaeolum sp.), approximately 5 cm tall, were transplanted into sandy loam soil in 3-inch clay pots and infested with 25–50 black bean aphids of mixed ages. 24 hours later, they were sprayed, to the point of runoff, with 50—50 acetone-water solutions of the test chemicals. Treated plants were held in the greenhouse and mortality was recorded after 7 days. Test concentrations ranged from 0.05% down to that at which 50% mortality occurred. LD-50 values are expressed below in Table II under the heading "BA" in terms of percent of the test compound in the sprayed solution.

Salt-Marsh Caterpillar: Test compounds were diluted in a 50—50 acetone-water solution. Sections of curly dock (*Rumex crispus*) leaves, approximately 1 × 1.5 inches, were immersed in the test solution for 2–3 seconds and placed on a wire screen to dry. The dried leaves were placed in petri dishes containing a moistened piece of filter paper and infested with 5 second-instar salt-marsh larvae. Mortality of the larvae was recorded 48 hours later, and a piece of synthetic media was added to dishes containing survivors. These were then held for 5 additional days to observe for any delayed effects of the test chemicals.

Test concentrations ranged from 0.05% down to that at which approximately 50% mortality occurred. LD-50 values are expressed below in Table II under the heading "SMC" in terms of percent of the test compound in the solution.

Tobacco Budworm: Test compounds were diluted in a 50—50 acetone-water solution. Sections of Romaine lettuce (Latuca sativa) leaves, approximately 1×1.5 inches, were immersed in the test solutions for 2–3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. LD-50 values are expressed below in Table II under the heading "TBW" in terms of percent of the test compound in the solution.

Acaricidal Evaluation Tests

The two-spotted mite (2-SM) *tetranychus urticae* (Koch) was employed in tests for miticides. The tests procedure was as follows:

Pinto bean plants (*Phaseolus sp.*) approximately 10 cm tall, were transplanted into sandy loam soil in 3-inch clay pots and thoroughly infested with two-spotted mites of mixed ages and sexes. 24 hours later, the infested plants were inverted and dipped for 2-3 seconds in 50—50 acetone-water solutions of the test chemicals. Treated plants were held in the greenhouse, and 7 days later mortality was determined for both the adult mites and the nymphs hatching from eggs which were on the plants at the time of treatment. Test concentrations ranged from 0.05% down to that at which 50% mortality occurred. LD-50 values are expressed below in Table II under the headings "2SM-PE" (i.e., post-embryonic) and "2SM-Eggs", in terms of percent concentration of the test compound in the solution.

Systematic Evaluation Test

This test evaluates the root absorption and upward translocation of the candidate systemic compound. The two-spotted mite (2SM) *Tetranychus urticae*, (Koch) and the Bean Aphid (BA) - *Aphis fabae* (Scop.) were employed in the test for systemic activity. Tests were conducted as follows:

Two-Spotted Mite: Test chemicals were dissolved in acetone and aliquots diluted in 200 cc of water in glass bottles. 2 pinto bean plants (*Phaseolus sp.*), with expanded primary leaves, were supported in each bottle by cotton plugs, so that their roots and stems were immersed in the treated water. The plants were then infested with 75–100 two-spotted mites of various ages and sexes. One week later the mortality of the adult mites and nymphs was recorded. Test concentrations in the medium ranged from 10 ppm down to that at which 50% mortality occurred.

Black Bean Aphid: Test chemicals were diluted in acetone and aliquots thoroughly mixed into 500 grams of dry, sandy loam soil. The treated soil was placed in a pint-sized carton and a nasturium plant (*Tropaeolum sp.*) approximately 5 cm tall was transplanted into each carton. The plants were then infested with approximately 25 black bean aphids of mixed ages and placed in the greenhouse. 7 days later mortality was recorded. Test concentrations ranged from 10 ppm down to that at which aproximately 50% mortality occurred.

LD-50 values are expressed below in Table II under the headings "2SM-S" and "BA(S)" respectively, in terms of percent concentration of the test compound.

Table II

| Compound No. | HF ($\mu$g) | GR (%) | LB (%) | BA (ppm) | BA(S) (%) | SMC (%) | TBW (%) | 2-SM P.E. (%) | 2-SM Eggs (ppm) | S |
|---|---|---|---|---|---|---|---|---|---|---|
| 1 | 80 | >0.1 | >.05 | .005 | 0.8 | >.05 | >0.1 | >.05 | <.05 | — |
| 2 | 100 | .05 | .05 | .008 | 0.8 | >.05 | >0.1 | .05 | .05 | — |
| 3 | 100 | >0.1 | .01 | .008 | 3 | >.05 | >0.1 | .05 | <.05 | 10 |
| 4 | 10 | 0.1 | .01 | .003 | 0.5 | >.05 | 0.1 | <.05 | <.05 | 8 |
| 5 | 50 | >0.1 | .03 | .008 | 3 | >.05 | >0.1 | <.05 | <.05 | 10 |
| 6 | 9 | .05 | .008 | .003 | 0.3 | >.05 | >0.1 | <.05 | <.05 | 5 |
| 7 | >100 | >0.1 | >.05 | .008 | 3 | >.05 | >0.1 | .05 | <.05 | 10 |

The compounds of this invention are generally embodied into a form suitable for convenient application. For example the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents, such as sesame oil, xylene range solvents, heavy petroleum, etc.; water, emulsifying agents; surface active agents; talc; pyrophyllite, diatomite; gypsum; clays, propellants, such as dichlorodifluoromethane, etc. If desired, however, the active compounds can be applied directly to feedstuffs, seeds, etc., upon which the pests feed. When applied in such a manner, it will be advantageous to use a compound which is not volatile. In connection with the activity of the presently disclosed pesticidal compounds, it should be fully understood that it is not necessary that they be active as such. The purpose of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise between about 0.01 and about 80% by weight of the composition.

What is claimed is:

1. A compound having the formula

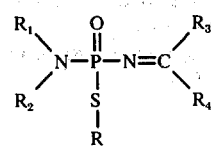

in which R and $R_1$ are lower alkyl, $R_2$ and $R_3$ are independently hydrogen or lower alkyl, provided that at least one of $R_2$ and $R_3$ is lower alkyl, and $R_4$ is amino or lower alkoxy.

2. A compound according to claim 1 in which R is methyl.

3. A compound according to claim 1 in which $R_2$ and $R_3$ are both lower alkyl.

4. A compound according to claim 1 in which R and $R_1$ are both methyl.

5. A compound according to claim 1 in which $R_4$ is amino.

6. A compound according to claim 1 in which $R_4$ is lower alkoxy.

7. A compound according to claim 1 in which R, $R_1$, and $R_2$ are each methyl, $R_3$ is hydrogen and $R_4$ is ethoxy.

8. A compound according to claim 1 in which R, $R_1$, $R_2$ and $R_3$ are each methyl and $R_4$ is ethoxy.

9. A compound according to claim 1 in which R, $R_1$, and $R_2$ are each methyl, $R_3$ is ethyl and $R_4$ is ethoxy.

10. A compound according to claim 1 in which R, $R_1$ and $R_2$ are each methyl, $R_3$ is hydrogen and $R_4$ is methoxy.

11. A compound according to claim 1 in which R, $R_1$ and $R_2$ are each methyl, $R_3$ is ethyl and $R_4$ is amino.

12. A compound according to claim 1 in which R, $R_1$ and $R_2$ are each methyl, $R_3$ is hydrogen and $R_4$ is amino.

13. A compound according to claim 1 in which R is methyl, $R_1$ is isopropyl, $R_2$ is hydrogen, $R_3$ is methyl and $R_4$ is ethoxy.

14. A method for controlling insects comprising applying to the insect or habitat thereof an insecticidally effective amount of the compound having the formula

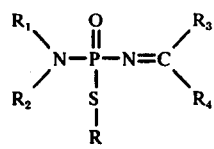

in which R and $R_1$ are lower alkyl, $R_2$ and $R_3$ are independently hydrogen or lower alkyl, provided that at least one of $R_2$ and $R_3$ is lower alkyl, and $R_4$ is amino or lower alkoxy.

15. A method according to claim 14 in which R is methyl.

16. A method according to claim 14 in which $R_2$ and $R_3$ are both lower alkyl.

17. A method according to claim 14 in which R and $R_1$ are both methyl.

18. A method according to claim 14 in which $R_4$ is amino.

19. A method according to claim 14 in which $R_4$ is lower alkoxy.

20. An insecticidal composition comprising (a) an insecticidally effective amount of the compound having the formula

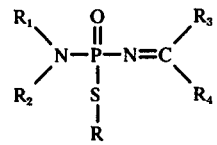

in which R and $R_1$ are lower alkyl, $R_2$ and $R_3$ are independently hydrogen or lower alkyl, provided that at least one of $R_2$ and $R_3$ is lower alkyl, and $R_4$ is amino or lower alkoxy; and (b) an inert carrier.

* * * * *